US010463669B2

(12) United States Patent
Jung et al.

(10) Patent No.: US 10,463,669 B2
(45) Date of Patent: Nov. 5, 2019

(54) COMPOSITION FOR TREATING OR PREVENTING LIVER CANCER

(71) Applicant: Seoul National University R&DB Foundation, Seoul (KR)

(72) Inventors: Guhung Jung, Seoul (KR); Eunkyong Ko, Seoul (KR); Yoon Jun Kim, Seoul (KR)

(73) Assignee: Seoul National University R&DB Foundation, Seoul (KR)

(*) Notice: Subject to any disclaimer, the term of this patent is extended or adjusted under 35 U.S.C. 154(b) by 0 days.

(21) Appl. No.: 15/998,556

(22) PCT Filed: Feb. 14, 2017

(86) PCT No.: PCT/KR2017/001575
§ 371 (c)(1),
(2) Date: Aug. 15, 2018

(87) PCT Pub. No.: WO2017/142283
PCT Pub. Date: Aug. 24, 2017

(65) Prior Publication Data
US 2019/0160073 A1    May 30, 2019

(30) Foreign Application Priority Data

Feb. 15, 2016 (KR) .................. 10-2016-0017187

(51) Int. Cl.
A61K 31/52    (2006.01)
A61K 9/16     (2006.01)
A61K 9/20     (2006.01)
A61K 9/48     (2006.01)
A61K 31/517   (2006.01)
A61P 35/00    (2006.01)

(52) U.S. Cl.
CPC ............ *A61K 31/52* (2013.01); *A61K 9/16* (2013.01); *A61K 9/20* (2013.01); *A61K 9/48* (2013.01); *A61K 31/517* (2013.01); *A61P 35/00* (2018.01)

(58) Field of Classification Search
CPC ........ A61K 31/517; A61K 31/52; A61K 9/16; A61K 9/20; A61K 9/48; A61P 35/00
See application file for complete search history.

(56) References Cited

FOREIGN PATENT DOCUMENTS

WO    WO-2016097314 A1 * 6/2016 ............ C07D 473/34

OTHER PUBLICATIONS

Yang et al. (Clinical Cancer Res: 21 (7), 2015, pp. 1537-1542 (Year: 2015).*

* cited by examiner

*Primary Examiner* — Savitha M Rao
(74) *Attorney, Agent, or Firm* — Vorys, Sater, Seymour and Pease LLP; Mih Suhn Koh

(57) ABSTRACT

The present application relates to a pharmaceutical composition containing compound 5-fluoro-3-phenyl-2-[(1S)-1-(7H-purin-6-ylamino)propyl]-4-3H)-quinazolinone, and a pharmaceutically acceptable salt thereof for preventing and treating liver cancer, and the composition of the present application inhibits ROS-PI3K-AKT-TERT signal transduction, and thus can be favorably used in the treatment of a liver cell cancer, in which a protein involved in the signal transduction is overexpressed, especially, advanced liver cell cancer.

9 Claims, 4 Drawing Sheets
Specification includes a Sequence Listing.

SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: FAM-labeled telomere PNA probe TelGFAM

<400> SEQUENCE: 1
ttagggttag ggttaggg                                         18

<210> SEQ ID NO 2
<211> LENGTH: 18
<212> TYPE: DNA
<213> ORGANISM: Artificial Sequence
<220> FEATURE:
<223> OTHER INFORMATION: FAM-labeled centromere PNA probe CentFAM

<400> SEQUENCE: 2
aaactagaca gaagcatt                                         18

<210> SEQ ID NO 3
<211> LENGTH: 18
<212> TYPE: DNA
<213> ORGANISM: Artificial Sequence
<220> FEATURE:
<223> OTHER INFORMATION: Cy3-labeled telomere PNA probe TelCCy3

<400> SEQUENCE: 3
ccctaaccct aaccctaa                                         18

<210> SEQ ID NO 4
<211> LENGTH: 18
<212> TYPE: DNA
<213> ORGANISM: Artificial Sequence
<220> FEATURE:
<223> OTHER INFORMATION: beta-actin TERT forward primer

<400> SEQUENCE: 4
gccttcaaga gccacgtc                                         18

<210> SEQ ID NO 5
<211> LENGTH: 18
<212> TYPE: DNA
<213> ORGANISM: Artificial Sequence
<220> FEATURE:
<223> OTHER INFORMATION: beta-actin TERT reverse primer

<400> SEQUENCE: 5
ccacgaactg tcgcatgt                                         18

<210> SEQ ID NO 6
<211> LENGTH: 21
<212> TYPE: DNA
<213> ORGANISM: Artificial Sequence
<220> FEATURE:
<223> OTHER INFORMATION: beta-Actin forward primer

<400> SEQUENCE: 6
gcaaagacct gtacgccaac a                                     21

<210> SEQ ID NO 7
<211> LENGTH: 18
<212> TYPE: DNA
<213> ORGANISM: Artificial Sequence -continued

```
<220> FEATURE:
<223> OTHER INFORMATION: beta-Actin reverse primer

<400> SEQUENCE: 7
tgcatcctgt cggcaatg                                                 18

<210> SEQ ID NO 8
<211> LENGTH: 18
<212> TYPE: DNA
<213> ORGANISM: Artificial Sequence
<220> FEATURE:
<223> OTHER INFORMATION: beta-catenin interaction site for ChIP forward
      primer

<400> SEQUENCE: 8
tcccgggtcc ccggccca                                                 18

<210> SEQ ID NO 9
<211> LENGTH: 20
<212> TYPE: DNA
<213> ORGANISM: Artificial Sequence
<220> FEATURE:
<223> OTHER INFORMATION: beta-catenin interaction site for ChIP reverse
      primer

<400> SEQUENCE: 9
cctcgcggta gtggctgcgc                                               20

<210> SEQ ID NO 10
<211> LENGTH: 20
<212> TYPE: DNA
<213> ORGANISM: Artificial Sequence
<220> FEATURE:
<223> OTHER INFORMATION: TERT intron for ChIP forward primer

<400> SEQUENCE: 10
tgagggctga gaaggagtgt                                               20

<210> SEQ ID NO 11
<211> LENGTH: 20
<212> TYPE: DNA
<213> ORGANISM: Artificial Sequence
<220> FEATURE:
<223> OTHER INFORMATION: TERT intron for ChIP reverse primer

<400> SEQUENCE: 11
cacgatagac gacgacctca                                               20
```

COMPOSITION FOR TREATING OR PREVENTING LIVER CANCER

CROSS-REFERENCE TO RELATED APPLICATIONS

This application is the National Stage entry of PCT/KR2017/001575, filed on Feb. 14, 2017, which claims priority to Korean Application Number 10-2016-0017187, filed on Feb. 15, 2016, which are incorporated herein by reference in their entireties.

SEQUENCE LISTING

The Sequence Listing submitted in text format (.txt) filed on Feb. 12, 2019, named "SequenceListing.txt", created on Jan. 11, 2019 (2.45 KB), is incorporated herein by reference.

TECHNICAL FIELD

The present invention relates to a composition for prevention and treatment of liver cancer.

BACKGROUND ART

Liver cancer is the second leading cause of death related to cancer worldwide, and hepatocellular carcinoma (HCC) accounts for between 85% and 90% of liver cancer. Almost 70% to 80% of hepatocellular carcinoma is discovered only after it is progressed into an advanced stage. At present, there is only Sorafenib as a medicine which is approved as a therapeutic agent specific to advanced hepatocellular carcinoma.

Major cause of HCC is liver cirrhosis. Since there are many causes of having liver cirrhosis such as hepatitis caused by hepatitis viruses (i.e., HBV or HCV), alcohol consumption, or non-alcoholic fatty liver, it is difficult to lay out a strategic plan for treating a patient with HCC based on personal history of liver cirrhosis alone.

It has been known that various pathways including Wnt-β-catenin pathway, p53-Rb pathway, chromatin remodeling and phosphatidylinositol 3-kinase (PI3K)-AKT are related with an onset of HCC (El-Serag H B, Rudolph K L. Hepatocellular carcinoma: epidemiology and molecular carcinogenesis. Gastroenterology. 2007; 132: 2557-76; Schulze K, Imbeaud S, Letouze E, Alexandrov L B, Calderaro J, Rebouissou S, et al. Exome sequencing of hepatocellular carcinomas identifies new mutational signatures and potential therapeutic targets. Nat Genet. 2015; 47: 505-11). However, in spite of the results of those studies, the major determinant of the advance from early HCC to advanced HCC (i.e., GII HCC and GIII HCC) is yet to be identified.

Idelalisib is a PI3K inhibitor and a medicine approved by US FDA and European Medicines Agency as a therapeutic agent for late relapsed Non-Hodgkin's B-cell lymphoma. Upon binding to the ATP-binding site of p110δ, this inhibitor inactivates the PI3K-AKT signal transduction pathway. Activation of the PI3K pathway is mediated by class I PI3K catalytic isotypes p110α, p110β, p110δ, and p110γ. p110δ is predominantly expressed in hematopoietic stem cells, and the PI3K-AKT signal transduction basically contributes to immune cell proliferation and stimulation of related cytokines and chemokines. Accordingly, with regard to idelalisib, until now the focus is on cell survival, in particular, death of immune cells.

Korean Patent Application Publication No. 10-2014-0022836 is related to combination therapies for hematologic malignancies, and it discloses a use of idelalisib for treating lymphoblastic leukemia. However, nothing is known about the role played by idelalisib in liver cancer, in particular, advanced hepatocellular carcinoma, and development of a therapeutic agent for advanced hepatocellular carcinoma is in need.

SUMMARY OF INVENTION

Technical Problem

The present invention aims to provide a pharmaceutical composition for suppressing hepatocellular carcinoma proliferation based on inhibition of TERT expression and telomerase in hepatocellular carcinoma cell line.

Solution to Problem

According to one aspect of the present invention, provided is a pharmaceutical composition for prevention and treatment of hepatocellular carcinoma comprising 5-fluoro-3-phenyl-2-[(1S)-1-(7H-purin-6-ylamino)propyl]-4(3H)-quinazolinone or a pharmaceutically acceptable salt thereof.

In one embodiment according to the present invention, the hepatocellular carcinoma is hepatocellular carcinoma in which ROS level is increased so that PI3K isotype p110δ is overexpressed.

In another embodiment according to the present invention, the hepatocellular carcinoma is advanced hepatocellular carcinoma, which can be determined by a method for classifying liver cancer based on several stages of progression known in the pertinent art. Although it is not limited thereto, the advanced hepatocellular carcinoma is hepatocellular carcinoma at stage II or higher stage on the basis of the hepatocellular carcinoma TNM (tumor-node-metastasis) by LCSGJ (Liver Cancer Study Group of Japan). Alternatively, the advanced hepatocellular carcinoma is hepatocellular carcinoma of grade II or higher grade on the basis of the Edmondson-Steiner grading system as a method for histological grading of tumor differentiation.

In another embodiment, hepatocellular carcinoma can be treated by the pharmaceutical composition of the present invention based on inhibition of the ROS-PI3K-AKT-TERT signal transduction.

According to another aspect of the present invention, provided is a kit for in vivo or in vitro suppression of the expression of PI3K isotype p110δ in liver cancer cells or liver cancer cell lines comprising 5-fluoro-3-phenyl-2-[(1S)-1-(7H-purin-6-ylamino)propyl]-4(3H)-quinazolinone or a pharmaceutically acceptable salt thereof.

In one embodiment, the liver cancer cells for which the kit of the present invention is effective have high ROS level.

According to another aspect of the present invention, provided is a kit for in vivo or in vitro suppression of the ROS-PI3K-AKT-TERT signal transduction in liver cancer cells or liver cancer cell lines comprising 5-fluoro-3-phenyl-2-[(1S)-1-(7H-purin-6-ylamino)propyl]-4(3H)-quinazolinone or a pharmaceutically acceptable salt thereof.

According to another aspect, the present invention relates to a method for suppression of the expression of PI3K isotype p110δ in liver cancer cells including treating the liver cancer cells with 5-fluoro-3-phenyl-2-[(1S)-1-(7H-purin-6-ylamino)propyl]-4(3H)-quinazolinone or a salt thereof.

According to another aspect, the present invention provides a method for suppression of the ROS-PI3K-AKT-TERT signal transduction pathway in liver cancer cells including treating the liver cancer cells with 5-fluoro-3-phenyl-2-[(1S)-1-(7H-purin-6-ylamino)propyl]-4(3H)-quinazolinone or a salt thereof.

In one embodiment, the liver cancer cells are cells having increased ROS level and they encompass both liver cancer cell lines and liver cancer cells or tissues.

According to still another aspect, the present invention provides a method for treatment of hepatocellular carcinoma including administering a pharmaceutically effective amount of the compound 5-fluoro-3-phenyl-2-[(1S)-1-(7H-purin-6-ylamino)propyl]-4(3H)-quinazolinone or a pharmaceutically acceptable salt thereof to a subject who is in need of a treatment of hepatocellular carcinoma.

In one embodiment according to the present invention, the hepatocellular carcinoma is hepatocellular carcinoma in which ROS level is increased so that PI3K isotype p110δ is overexpressed.

In another embodiment according to the present invention, the hepatocellular carcinoma is advanced hepatocellular carcinoma, which can be determined by a method for classifying liver cancer based on several stages of progression known in the pertinent art, and although it is not limited thereto, the advanced hepatocellular carcinoma is hepatocellular carcinoma at stage II or higher stage on the basis of the hepatocellular carcinoma TNM (tumor-node-metastasis) by LCSGJ (Liver Cancer Study Group of Japan), or alternatively, the advanced hepatocellular carcinoma is hepatocellular carcinoma of grade II or higher grade on the basis of the Edmondson-Steiner grading system as a method for histological grading of tumor differentiation.

Effect of the Invention

By inhibiting the PI3K-AKT-TERT signal transduction which is activated by ROS in hepatocellular carcinoma (HCC) to lower the TERT expression and reduce the telomere length, the pharmaceutical composition of the present invention can suppress the tumor proliferation. In particular, the pharmaceutical composition can be advantageously used for the treatment of advanced liver cancer or malignant liver cancer in which ROS level is increased so that the expression of PI3K isotype p110δ is increased.

BRIEF DESCRIPTION OF DRAWINGS

FIGS. 1A to 1C illustrate dose-dependent inhibition by idelalisib in two HCC cell lines with activated AKT (i.e., activated PI3K/AKT signal transduction) and also in non-liver cancer cell line derived from normal liver (i.e., inactivated PI3K/AKT signal transduction). Huh7 cells (FIG. 1A) and Hep3B cells (FIG. 1B), which are the two HCC cell lines, and non-liver cancer cell line THLE-3 cells (FIG. 1C) derived from normal liver were treated with idelalisib in a predetermined dose range, and the cell proliferation was analyzed by MTS assay. The immunostaining image shown in the box indicates that p110δ expression selectively targeted by idelalisib is higher in the HCC cells than the THLE-3 cells. The scale bar equals 10 μm. FIGS. 1D to 1F illustrate target inhibition and downstream signal transduction after the treatment with idelalisib in the HCC cell line model in which AKT is activated and non-liver cancer cell line derived from normal liver in which AKT is inactivated. FIGS. 1G to 1I illustrate shortened telomere in the HCC cell line after the treatment with idelalisib. The telomere length was quantified by telomere Southern blot (FIG. 1G), immunoFISH (FIGS. 1H, 1J, and 1L), and quantitative PCR (FIGS. 1I, 1K, and 1M). The T/S ratio indicates ratio of the telomere repeat copy number to single-copy gene copy number. POC represents percentage of a control group. Numbers described in the data represent mean±SEM (n=4 per group); according to **t-test, P<0.01.

FIG. 2A illustrates the p110 isotype mRNA level in Huh7, Hep3B, and THLE-3 cells. FIG. 2B illustrates the p110 isotype mRNA level in Huh7, Hep3B, and THLE-3 cells after a treatment with hydrogen peroxide ($H_2O_2$). FIGS. 2C to 2E illustrates percentage of cell viability (bright blue), telomere fluorescence (red), TERT expression (black) in the presence of $H_2O_2$ and ROS scavenger NAC at various concentrations, and percentage of TERT protein immunoassay. Average length of telomere is determined by Flow-FISH. Huh7 cells (FIG. 2C), Hep3B cells (FIG. 2D), and THLE-3 cells (FIG. 2E). POC represents percentage of a control group and NAC represents N-acetylcysteine. FIGS. 2F to 2H illustrate target inhibition and downstream signal transduction after the treatment with idelalisib in 300 μmol/L $H_2O_2$-treated HCC cell line and 150 μmol/L $H_2O_2$-treated THLE-3 cells. The TERT expression was normalized with β-actin. POC represents percentage of a control group. FIGS. 2I to 2K illustrate the telomere activity in 300 μmol/L $H_2O_2$-treated HCC cell line and 150 μmol/L $H_2O_2$-treated THLE-3 cells, in the presence or absence of idelalisib treatment. Numbers described in the data represent mean±SEM (n=4 per group). P value based on comparison between the indicated treatment group and control group is as follows; according to t-test, P<0.01, *P<0.001, and ****P<0.0001.

FIGS. 3A to 3C illustrate ChIP using β-catenin interaction site of TERT promoter in 300 μmol/L $H_2O_2$-treated or mock-treated Huh7 cells in the presence or absence of PI3K inhibitor idelalisib (FIG. 3A), AKT inhibitor perifosine (FIG. 3B), or GSK3β inhibitor XI (FIG. 3C). Numbers represent mean±SEM (n=4 per group); according to t-test, P<0.01 and *P<0.001. FIG. 3D shows a representative image of a nude mouse on Week 6 after transplanting mock-treated Huh7 cells, 300 μmol/L $H_2O_2$-treated Huh7 cells, and Huh7 cells treated with both of 300 μmol/L $H_2O_2$ and 25 μmol/L idelalisib. The encircled area illustrates tumor. The scale bar equals 10 cm. FIG. 3E is a graph illustrating mean tumor volume (W) of a mouse that is determined every week. Compared to a mouse injected with the same number of the cells that have been treated with both of $H_2O_2$ and idelalisib, P value was determined by using one-sided rank test. Number of the mouse was as follows; 4 for the mock treatment, 5 for the $H_2O_2$ treatment, and 4 for the treatment with both of $H_2O_2$ and idelalisib.

FIG. 4A illustrates p110δ expression in GI, GII, and GIII HCC tumor tissues (n=98). FIG. 4B illustrates mean TERT expression (horizontal line) in HCC tissue (n=98) in which p110δ mRNA is present either at high level or at low revel. FIG. 4C illustrates recurrence-free survival ratio proportional to p110δ expression in which n=84. The samples were divided into two groups based on mean p110δ expression. The survival ratio was measured by using Kaplan-Meier method, and comparison of the survival ratio was made by using a log-rank test. Corresponding hazard ratio (HR) was shown by a survival plot. FIG. 4D illustrates a molecular model in which potential function of ROS and the inhibitor for PI3K and AKT in advanced HCC is shown. Namely, it is shown that, as the ROS level increases as a result of activation of the AKT signal transduction in advanced HCC, up-regulation of TERT is yielded. AKT activation suppresses the GSK3β activity, while inactivation of GSK3β causes continuous accumulation of β-catenin protein in nucleus. As β-catenin binds to TERT promoter, TERT expression increases so that telomere elongation is yielded. RNA Pol II represents RNA polymerase II.

DESCRIPTION OF EMBODIMENTS

The present invention is based on findings that, among PIK3 isotypes, p110δ type is particularly overexpressed by ROS in hepatocellular carcinoma, in particular, hepatocellular carcinoma of advanced stage, and effective treatment of hepatocellular carcinoma, in particular, hepatocellular carcinoma of advanced stage can be achieved by suppressing the overexpression.

Accordingly, the present invention relates to a novel use of the compound 5-fluoro-3-phenyl-2-[(1S)-1-(7H-purin-6-ylamino)propyl]-4(3H)-quinazolinone (idelalisib) for treatment of hepatocellular carcinoma based on the elucidation of an onset mechanism of hepatocellular carcinoma.

According to one embodiment, the present invention relates to a pharmaceutical composition for prevention and treatment of hepatocellular carcinoma comprising the compound 5-fluoro-3-phenyl-2-[(1S)-1-(7H-purin-6-ylamino)propyl]-4(3H)-quinazolinone.

The compound "5-fluoro-3-phenyl-2-[(1S)-1-(7H-purin-6-ylamino)propyl]-4(3H)-quinazolinone" of the present invention is also called idelalisib, and the compound and a method for producing the compound are described in International Publication No. WO 2012/152210, which is incorporated herein by reference.

Figure 1:
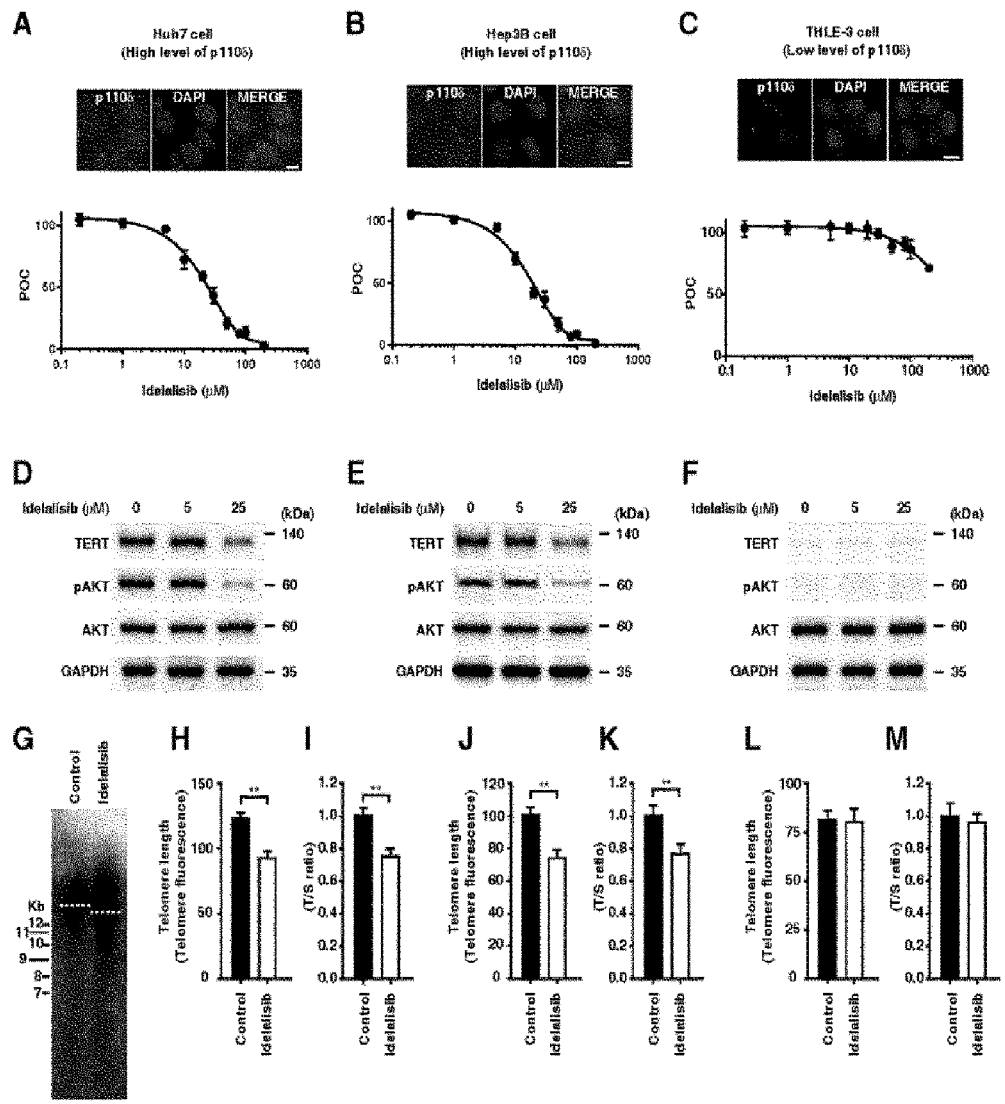
FIG. 1 shows that proliferation of HCC cells, PI3K-AKT-TERT signal transduction, and maintaining telomere length are inhibited by idelalisib according to one embodiment of the present invention.

According to one examples of the present invention, it is found that the compound of the present invention, which is a PI3K-Akt inhibitor, in particular, selective p110δ kinase inhibitor, has an effect of not only inhibiting the proliferation of Huh7 cells and Hep3b cells (FIGS. 1A and 1B), which are HCC cell lines, but also anti-telomerase effect of inhibiting telomere length elongation by inhibiting the expression of TERT (telomerase reverse transcriptase).

The composition of the present invention binds to the ATP-binding site of p110δ, thus inactivating the PI3K-AKT signal transduction pathway. By activating downstream kinases like AKT, PI3K plays an essential role for regulating cell growth, proliferation, and metabolism. Activation of the PI3K pathway is mediated by Class I PI3K catalytic isotypes p110α, p110β, p110δ, and p110γ, in which the enzymes of said class phosphorylate phosphatidylinositol 4,5-bisphosphate (PIP2) to produce phosphatidylinositol 3,4,5-bisphosphate (PIP3), which is the second essential messenger material.

Figure 2:
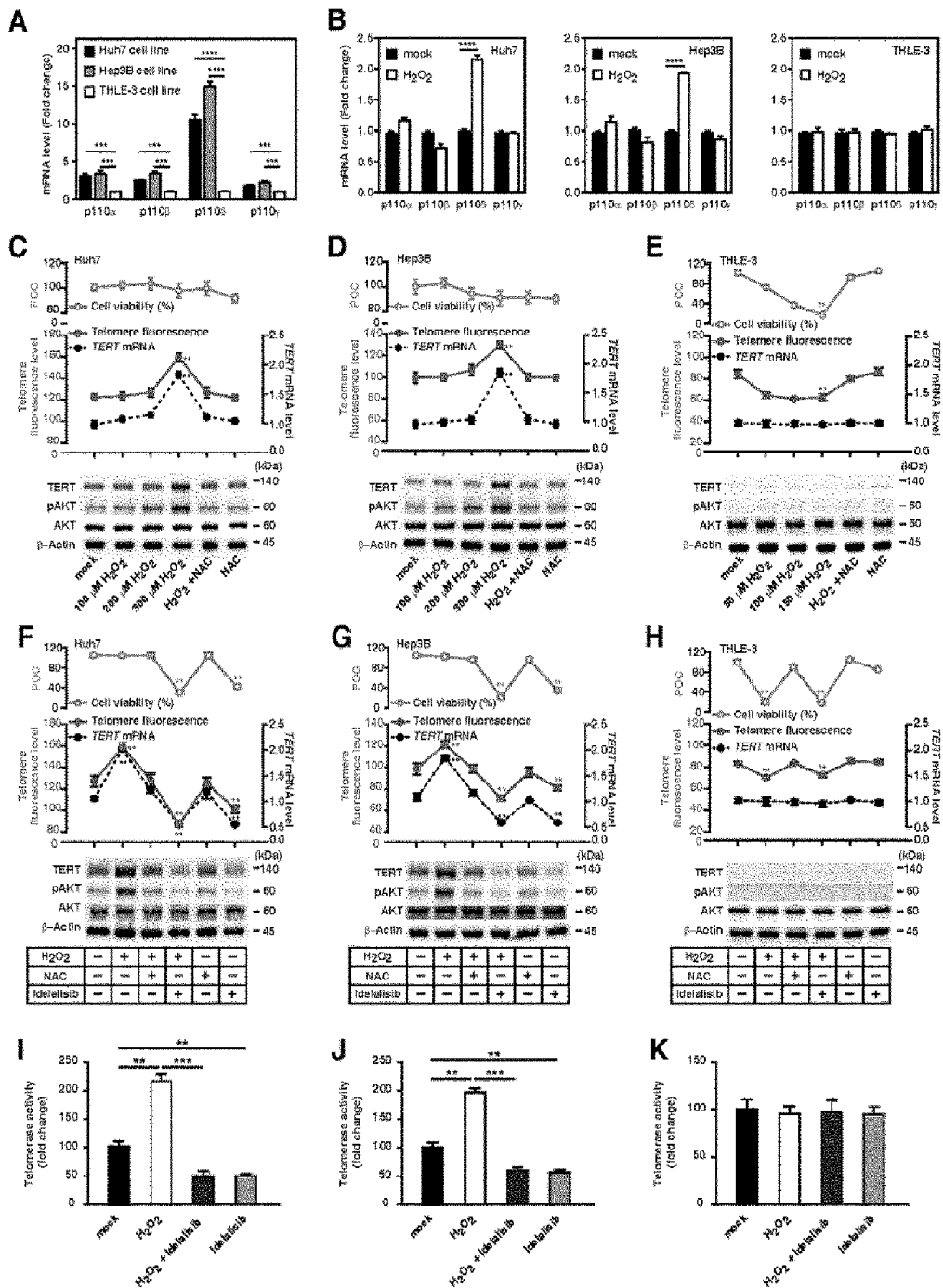
FIG. 2 shows that, in the HCC cells, ROS accelerates telomere elongation and activation of PI3K-AKT-TERT signal transduction while idelalisib suppresses the ROS-mediated PI3K-AKT-TERT signal transduction activation.

In another embodiment of the present invention, it was confirmed that the composition of the present invention suppresses the PI3K-AKT-TERT signal transduction that is activated by ROS (Reactive Oxygen Species) (FIG. 2). In cancer cells, the PI3K-AKT signal transduction pathway is over-activated by ROS. However, the activation of the aforementioned pathway can be inhibited by the composition of the present invention.

Figure 3:
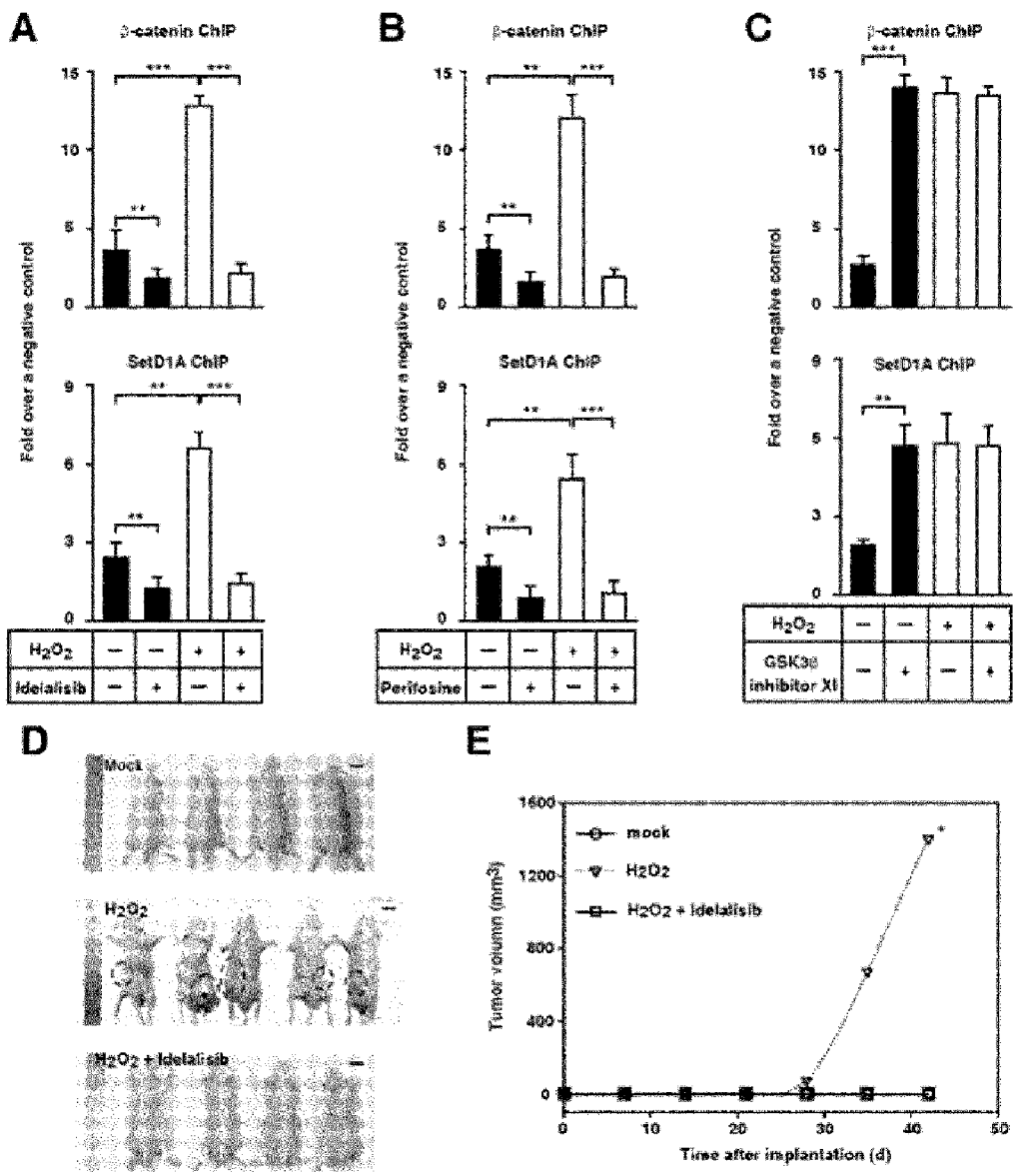
FIG. 3 shows that activation of ROS-PI3K-AKT β-catenin-TERT is inhibited by a PI3K-AKT inhibitor.
Figure 4:
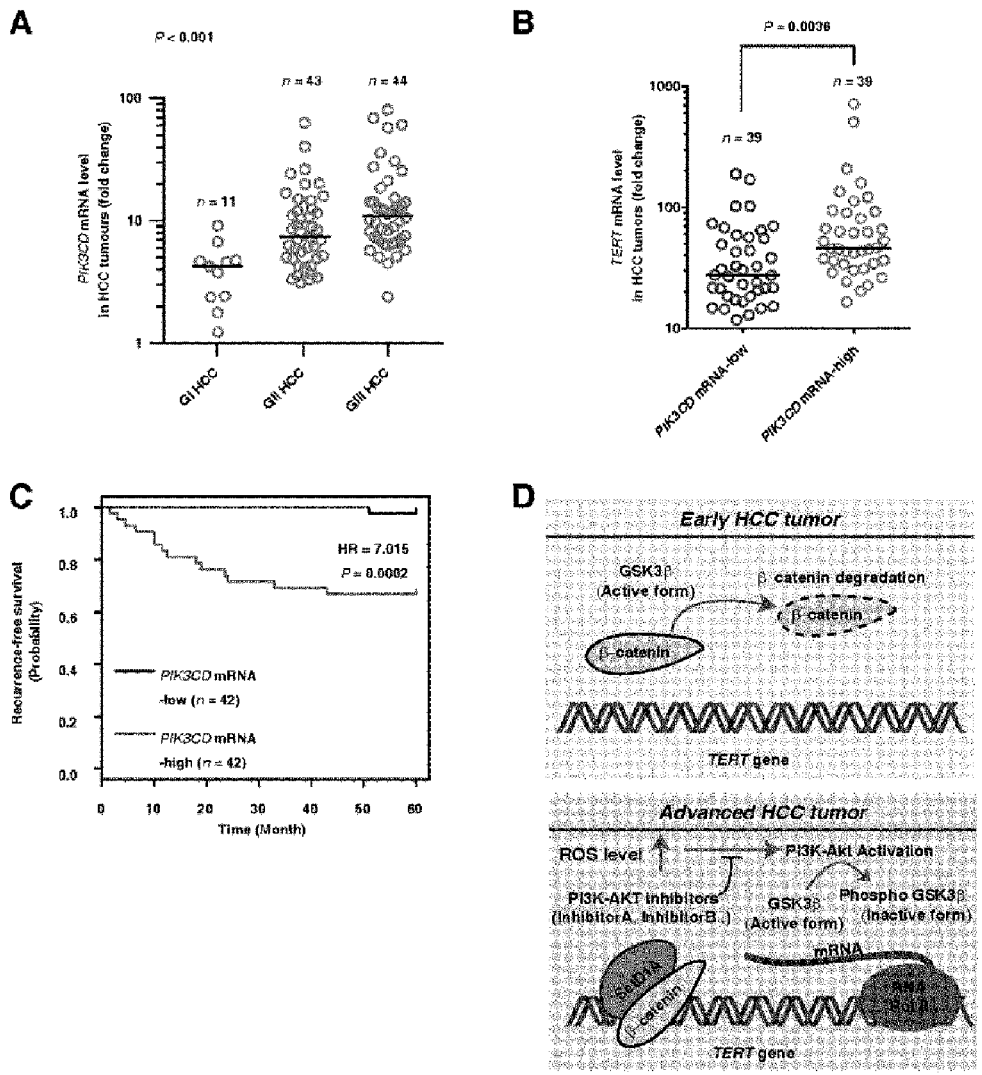
FIG. 4 shows that the TERT expression and low survival ratio in a HCC patient and HCC tumor tissues have positive relationship with the idelalisib-specific molecule p110δ expression.

It was also confirmed in another embodiment of the present invention that the composition of the present invention can suppress the activation of ROS-PI3K-AKT-βcatenin-TERT (FIG. 3). It was confirmed in the present invention that, as the PI3K-Akt signal transduction is over-activated by ROS, expression of β-catenin in nucleus increases, thus yielding increased TERT expression and elongation of telomere (FIGS. 3C and 4).

When the telomerase as an enzyme responsible for telomere elongation is inhibited, a telomere becomes shorter, each time a cell divides, and it eventually leads to growth stoppage, ageing, and death of a cell. The telomere shortening can be also caused by oxidative stress, and it is mediated by an intracellular increase of reactive oxygen species (ROS) in vivo. However, during a progress from early HCC to advanced HCC, the telomere is elongated instead of being shortened as the ROS level increases. During the advance process of various human tumors, the TERT (telomerase reverse transcriptase)-mediated activity allows unlimited proliferation of tumor cells by increasing the telomere length, and this phenomenon is preserved in HCC tumors. In one embodiment of the present invention, it was found that, according to inhibition of PI3K-AKT signal transduction, the telomerase expression is inhibited so that the telomere elongation is inhibited. As such, the present invention relates to a pharmaceutical composition for prevention and treatment of hepatocellular carcinoma comprising 5-fluoro-3-phenyl-2-[(1S)-1-(7H-purin-6-ylamino)propyl]-4(3H)-quinazolinone as an anti-telomerase.

As used herein, the term "hepatocellular carcinoma" indicates primary malignant tumor occurring originally in liver tissue, which is found in a patient having a risk factor like alcohol abuse, viral hepatitis, and compensated liver disease. Hepatocellular carcinoma accounts for 90% or more of entire liver cancers. 40% to 80% of the patients have a recurrence, mostly in liver. However, it may also occur in lung, lymph node, inside wall enclosing abdominal cavity, mediastinum, and cancers occurring in those areas are also included in the present invention.

In one embodiment of the present invention, use is made for a treatment of advanced liver cancer or malignant liver cancer, in particular. The classification based on the advance stage of liver cancer of the present invention is well known in the pertinent art, and reference can be made, for example, to Edmondson-Steiner grading system (Pirisi M et al., Arch Pathol Lab Med. 2010 December; 134 (12): 1818-22), which is a method for histological grading of tumor differentiation. According to the system, hepatocellular carcinoma for which the composition of the present invention is shown to be effective is hepatocellular carcinoma of grade II or higher grade among hepatocellular carcinomas that are classified into 1 to 4 grades. It is also possible that reference is made to American Joint Committee on Cancer (AJCC) TNM Staging for Liver Tumors (7th ed., 2010) or the recent version of HCC TNM (Tumor node metastasis) staging by Liver Cancer Study Group of Japan (LCSGJ)-T.

According to the above, hepatocellular carcinoma for which the composition of the present invention is shown to be effective is hepatocellular carcinoma at stage II or higher stage among hepatocellular carcinomas that are classified into 1 to 4 stages based on the advance stage thereof.

The terms "treatment", "alleviation", and "improvement" as used herein indicate all activities for ameliorating or altering in positive sense the symptoms of a metabolic disease by administering the composition of the present invention. Based on data suggested by Korean Academy of Medical Sciences, any person who has common knowledge in the art to which the present invention pertains would be aware of accurate criteria of a disease for which the composition of the present invention is effective and can determine the level of the improvement, enhancement, and treatment.

The pharmaceutically acceptable addition salt used in the present invention includes a pharmaceutically acceptable acid addition salt. The expression "pharmaceutically acceptable salt" means any organic or inorganic addition salt of a base compound, in which the adverse effect caused by the salt of does not impair the beneficial effect of a base compound at a concentration exhibiting relatively non-toxic and non-harmful effective activity to a patient. Examples of the acid include halogen acid such as hydrochloric acid or hydrobromic acid; inorganic acid such as sulfuric acid, nitric acid, or phosphoric acid, and; organic acid such as acetic acid, trifluoroacetic acid, propanoic acid, hydroxyacetic acid, lactic acid, pyruvic acid, oxalic acid, malonic acid, succinic acid (i.e., butane dioic acid), maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, or pamoic acid. Examples of a base salt form include an ammonium salt, an alkali salt, and an alkali earth metal salt such as lithium salt, sodium salt, potassium salt, magnesium salt, or calcium salt, and also a salt with an organic base such as benzathine salt, N-methyl-D-glucamine salt, or hydrabamine salt and a salt with an amino acid like arginine and lysine.

The therapeutic agent or pharmaceutical composition according to the present invention may be formulated, with a pharmaceutically acceptable carrier that is generally used, into suitable form. The expression "pharmaceutically acceptable" indicates a composition which is physiologically allowed and generally does not cause an allergic response such as stomach problem or nausea, or a similar response when administered to a human. Examples of the pharmaceutically acceptable carrier include water, suitable oil, physiological saline, and a carrier for parenteral administration like aqueous glucose and glycol, and a stabilizing agent and a preservative may be additionally included. Examples of a suitable stabilizing agent include an antioxidizing agent like sodium bisulfite, sodium sulfite, and ascorbic acid. Examples of a suitable preservative include benzalkonium chloride, methyl- or propyl-paraben, and chlorobutanol. Furthermore, depending on the administration method or formulation, the composition of the present invention may suitably contain a suspending agent, a solubilization aid, a stabilizing agent, an isotonic agent, a preservative, an anti-adsorbent, a surfactant, a diluent, an excipient, a pH modifying agent, an analgesic agent, a buffering agent, an anti-oxidant, or the like. In addition to those exemplified above, the pharmaceutically acceptable carriers and preparations that are suitable for the present invention are described in detail in the literature [Remington's Pharmaceutical Sciences, latest edition].

According to a method which can be easily carried out by a person who has common knowledge in the technical field to which the present invention pertains, the composition of the present invention can be produced in unit dosage form by preparing a formulation using a pharmaceutically acceptable carrier and/or excipient, or it can be produced by introduction to a multi-dosage container. In that case, the formulation may be in the form of oil or solution in aqueous medium, suspension or emulsion, or powder, granule, tablet, or capsule.

Method for administering the pharmaceutical composition of the present invention can be easily selected based on formulation, and the administration can be made to mammals including livestock and humans via various routes. For example, it can be formulated into a powder, a tablet, a pill, a granule, a sugar-coated pill, a hard or soft capsule, a liquid, an emulsion, a suspension, a syrup, an elixir, a preparation for external use, a suppository, a sterilized solution for injection or the like, and administered either systemically or topically, and also either orally or parenterally. Parenteral administration may be preferable, in particular.

Examples of the formulation for parenteral administration include a sterilized aqueous solution, a non-aqueous preparation, a suspension, an emulsion, a freeze-dried preparation, and a suppository. As for the non-aqueous solvent and suspension solvent, propylene glycol, polyethylene glycol, plant oil like olive oil, an injectable ester like ethyl oleate, and the like can be used. As for a suppository base, witepsol, macrogol, tween 61, cacao fat, laurin fat, glycerol, gelatin, and the like can be used.

The pharmaceutical composition of the present invention is administered in a pharmaceutically effective amount. The pharmaceutically effective amount enables obtainment of a desired effect, i.e., the effect of treating or ameliorating hepatocellular carcinoma, as a result of administering the compound of the present invention at predetermined dosage for a predetermined period of time. The dosage may vary within a broad range depending on weight, age, sex, or health state of a patient, diet, administration period, administration method, excretion rate, severeness of disorder, and the like. However, the effective dosage of the composition is generally 1 to 500 mg, and preferably 30 to 300 mg for an adult (60 kg), and it can be administered either once or several divided times per day. As for the dosage, reference can be made to dosage of existing pharmaceuticals. However, as the dosage may vary depending on various conditions, it would be evident to a person skilled in the pertinent art that a change can be made to the aforementioned dosage. Accordingly, the scope of the present invention is not limited by the aforementioned dosage in any sense. As for the number of administration, the administration can be made either once or several divided times per day within a desired range, and the administration period is not particularly limited, either.

According to another aspect, the present invention provides a method and a kit for in vivo or in vitro suppression of the expression of PI3K isotype p110δ or the ROS-PI3K-AKT-TERT signal transduction in liver cancer cells or liver cancer cell lines, in particular, liver cancer cells (cell lines) having overexpressed ROS, by using 5-fluoro-3-phenyl-2-[(1S)-1-(7H-purin-6-ylamino)propyl]-4(3H)-quinazolinone or a pharmaceutically acceptable salt thereof. As for the compound used for the method and kit and those related to the suppression of the aforementioned biological phenomena, reference can be made to the explanations that are given above.

As described in detail in the above, the compound of the present invention or a composition comprising the compound can be effectively used for the treatment of hepatocellular carcinoma.

According to still another aspect, the present invention relates to a method for treatment of hepatocellular carcinoma including administering a pharmaceutically effective amount of the compound 5-fluoro-3-phenyl-2-[(1S)-1-(7H-purin-6-ylamino)propyl]-4(3H)-quinazolinone or a pharmaceutically acceptable salt thereof to a subject who is in need of a treatment of hepatocellular carcinoma.

As for the pharmaceutically effective amount, administration method, types and treatment mechanism of hepatocellular carcinoma, or the like, reference can be made to the explanations that are given above.

Hereinbelow, examples are given to aid the understanding of the present invention. However, it is evident that the following examples are provided only for better understanding of the present invention, and the present invention is not limited to them.

EXAMPLES

Methods and Materials
Tumor Specimens

For all experiments in which human tissues are used, an approval from Institutional Review Board of Seoul National University was obtained (SNUIRB No. E1308/001-035). To have a gene expression analysis, 84 surgically removed and frozen samples of HCC tumor tissues and non-tumor liver tissue samples were analyzed. From 2005 to 2009 (133 paraffin-embedded samples) and from 2011 to 2013 (28 frozen tissue samples), and also from 2010 to 2013 (56 frozen tissue samples), each case was prospectively and continuously identified at St. Mary's Hospital of the Catholic University of Korea and Guro Hospital of Korea University (KU Guro Gene Bank 2013-020), respectively. Almost all tissue samples used in the present invention have been also used in previous studies of the inventors of the present invention. 93 Samples of the 133 paraffin-embedded samples and 19 samples of the 28 frozen tissue samples from St. Mary's Hospital, and 53 samples of the 56 frozen tissue samples from Guro Hospital were used (Ko E, et al., Seo H W, Jung E S, Kim B H, Jung G. The TERT promoter SNP rs2853669 decreases E2F1 transcription factor binding and increases mortality and recurrence risks in liver cancer. Oncotarget. 2015; Ko E, et al., Telomerase reverse transcriptase promoter methylation is related to a risk of recurrence in hepatocellular carcinoma. Hepatology. 2015). Of the 98 samples used for quantification at p110δ mRNA level for each of HCC GI, GII, and GIII, 14 frozen tissues have been also used for another study of the inventors of the present invention (Lim S O, et al., Hepatology. 2011; 53: 1352-62). The histological grade of tumor differentiation was defined according to Edmondson-Steiner grading system based on a tumor area showing the highest grade.

Cell Culture

HCC cell lines (Huh7 and Hep3B) were obtained from Korean Cell Line Bank (KCLB, Seoul, Korea). THLE-3 cell line (immortalized human liver endothelial cell line produced by infection with SV40 large T antigen) was obtained from ATCC (American Type Culture Collection). Cell line authentication by KCLB and ATCC was carried out by using DNA fingerprinting as a short tandem repeat analysis. All cell lines were tested for mycoplasma contamination. HCC cells were cultured in DMEM (Welgene, Gyeongsan-si, Korea) medium complemented with 10% fetal bovine serum (GenDepot, Barker, Tex., USA) in a humidified 5% $CO_2$ incubator at 37° C. As it has been recommended by the ATCC manual, THLE-3 cells were cultured in BEGM (Lonza) medium complemented with 10% fetal bovine serum in a humidified 5% $CO_2$ incubator at 37° C.

ROS Inducing Agent for PI3K, AKT, and GSK3β, ROS Scavenger and Treatment with Inhibitor Medium was exchanged every day, and the aforementioned cells were cultured for 4 days in 300 μmol/L hydrogen peroxide ($H_2O_2$) (Sigma Aldrich; H1009). In several experiments, the cells were treated for 1 hour with 5 mmol/L N-acetylcysteine (NAC) (Sigma Aldrich; A7250), 25 μmol/L idelalisib (LC Laboratoties, Woburn, Mass., USA; I-7447), 25 μmol/L perifosine (LC Laboratoties, Woburn, Mass., USA; P-6522), or 30 μmol/L GSK3β inhibitor (GSK3β inhibitor XI) (Santa Cruz; sc-204770) (31) before adding $H_2O_2$. Furthermore, sterilized distilled water (pH 7.0) was used as a negative control (i.e., mock treatment).

Flow FISH

Flow FISH was carried out as described before (Rufer N, et al., Nat Biotechnol. 1998; 16: 743-7) with few modifications. The cells were washed twice with cold PBS (phosphate-buffered saline) solution containing 0.1% w/v bovine serum albumin (BSA). Subsequently, the cells were re-suspended in hybridization buffer (70% deionized formamide (Amresco, Solon, Ohio, USA), 20 mmol/L TrisHCl [pH 6.8], 1% BSA, and 1 nmol/L FAM-labeled telomere PNA (telomere peptide nucleic acid) probe (TelGFAM: TTAGGGTTAGGGTTAGGG (SEQ ID NO:1) (Panagene, Daejeon, Korea), or 1 nmol/L FAM-labeled centromere PNA probe (CentFAM: AAACTAGACAGAAGCATT (SEQ ID NO:2) (Panagene). Volume of the hybridization buffer was adjusted to 100 μl per $10^5$ cells. Next, each sample was cultured for 10 minutes in a water bath at 85° C. Hybridization with telomere probe was carried out for 3 hours under dark conditions at room temperature, and each sample was washed with each washing solution (washing solution I: 70% deionized formamide, 10 mM TrisHCl [pH 6.8], 0.1% BSA, and 0.1% Tween 20; washing solution II: 0.1% BSA and 0.1% Tween 20 in PBS), and then cultured in a solution (0.1% BSA, 10 μg/mL RNase A, and 0.06 μg/mL 7-AAD in PBS) for 1 hour at 37° C. Total 15,000 to 20,000 nuclei were analyzed for the each separate culture. Telomere fluorescence intensity of the all nuclei at G1G0 phase of the cell cycle was measured by using BD FACS Calibur flow cytometer (Becton Dickinson, Franklin Lakes, N.J., USA) in which CELLQUEST software is used.

ImmunoFISH

The established ImmunoFISH protocol (Plentz R R, et al., Hepatology. 2007; 45: 968-76) was used with slight modifications. The paraffin-embedded section was subjected to de-paraffinization using xylene, and then rehydrated using ethanol gradient. Antigen retrieval was carried out by boiling in 100 mmol/L sodium citrate (pH 6.0) for 10 minutes in a microwave. After permeation of proteinase K (15 μg/mL in PBS [pH 7.4]) for 20 minutes at 37° C., 8-oxo-dG-specific antibody (1:100, Abcam, Cambridge, Mass., USA; ab62623) was subjected to 1% BSA dilution in PBS 0.1% Triton X-100 and cultured overnight at room temperature. After washing, the slide was treated with Alexa 647 secondary antibody for 1 hour. The sample was then fixed by using 4% formaldehyde and air dried. After denaturation for 6 minutes at 90° C., the sample was hybridized for 2 hours at dark place. In the hybridization solution, 70% formaldehyde in 2×SSC, 5% $MgCl_2$, 0.25% blocking reagent (Roche, Basel, Switzerland), 15.4 nmol/L of Cy3-labeled telomere PNA probe (TelCCy3: CCCTAACCCTAACCCTAA (SEQ ID NO: 3) (Panagene, Daejeon, Korea), and 18.4 nmol/L FAM-labeled centromere PNA probe(CentFAM: AAACTAGACAGAAGCATT (SEQ ID NO: 2) (Panagene) were contained. After washing, the slide was rinsed with PBS containing DAPI, and then sealed with a DAPI sealing agent (mounting medium) (Vector Laboratories, Burlingame, Calif., USA). Simultaneously, the inventors of the present invention carried out centromere staining as an internal control for telomere staining and 8-oxo-dG staining. It has been reported that the increased level of oxidative DNA adduct 8-oxo-2'-deoxyguanosine (8-oxo-dG), which is a molecular ROS marker, is shown in various tumor types including HCC. The telomere fluorescence level and 8-oxo-dG level indicate the ratio of telomere fluorescence intensity to centromere fluorescence intensity, and the ratio of 8-oxo-dG fluorescence intensity to centromere fluorescence intensity, respectively. For quantification of the telomere fluorescence intensity, centromere fluorescence intensity, and 8-oxo-dG fluorescence intensity, the same exposure time was employed. The telomere fluorescence level and 8-oxo-dG fluorescence level of tumor tissues were calculated by division of the fluorescence level in non-tumor tissues corresponding to 5 random fields. The image analysis was carried out by using Image-Pro plus 6.0 software (Media Cybernetics, Inc., Rockville, Md., USA).

Telomere Southern Blot

Telomere length was determined by using the non-radioactive chemical fluorescence TeloTAGGG telomere length assay (Roche; Cat. No. 12 209 136 001) according to the manual. Genomic DNA was separated from HCC cells using GeneJET Genomic DNA Purification Kit (Thermo Scientific; #K0721), and then 4 μg of the genomic DNA was digested for 16 hours at 37° C. with 20 units of Hinf 1 (Enzynomics) and Rsa 1 (Enzynomics). The digested DNA was subjected to 0.8% agarose gel electrophoresis, and then transferred to a positively charged nylon membrane using capillary transfer. The blotted DNA was hybridized for 16 hours at 42° C. with a digoxigenin (DIG)-labeled probe that is specific to the telomere repeat. After that, it was cultured for 30 minutes at room temperature with DIG-specific antibody conjugated to an alkaline phosphatase Measurement of Relative Telomere Length Based on Quantitative Real Time-PCR Based on quantitative PCR analysis using the genomic DNA extracted from cells, relative telomere repeat copy number (T) and single copy number (S) were determined, and the calculation was made like previous method in which T/S ratio is continuously modified (Cawthon R M. Telomere length measurement by a novel monochrome multiplex quantitative PCR method. Nucleic Acids Res. 2009; 37: e21).

Immunofluorescence Assay

In order to have visualization of p110δ expression level, p110δ-specific (1:500, Abcam; ab32401) antibody was used. After washing, the slide was sealed using a medium containing DAPI (Vector Laboratories). Image was obtained by using a confocal microscope (LSM 700; Carl Zeiss, Oberkochen, Germany). Image analysis was carried out by using Image-Pro plus 6.0 software (Media Cybernetics, Inc.)

TRAP (Telomerase Repeat Amplification Protocol) assay

To have quantitative determination of the telomerase activity, TRAP assay was carried out by using TRAPEZE® RT Telomerase Detection Kit (Millipore, Darmstadt, Germany; S7710). According to the manual, the whole protein extract (100 ng) was used for each reaction.

Determination of Gene Expression Level Using Quantitative Real Time-PCR

Total RNA was isolated using NucleoSpin® TriPrep Kit (Macherey-Nagel, Duren, Germany; 740966.250), and then, by using TOPscript™ RT Drymix (dT18) (Enzynomics, Daejeon, Korea; RT200), cDNA was synthesized from the total RNA of the cells which have been either mock-treated or treated with an indicated reagent. PCR was carried out by using TOPrealm qPCR 2×PreMIX (SYBR Green with high ROX) (Enzynomics, Daejeon, Korea; RT501M) and ABI Prism 7300 thermal cycler (Applied Biosystems, Foster City, Calif., USA). Gene expression was normalized with β-actin: TERT (forward primer: GCCTTCAAGAGC-CACGTC (SEQ ID NO:4); reverse primer: CCACGAACT-GTCGCATGT (SEQ ID NO:5)) (26) and β-Actin (forward primer: GCAAAGACCTGTACGCCAACA (SEQ ID NO:6); reverse primer: TGCATCCTGTCGGCAATG (SEQ ID NO:7)). To examine the primer specificity, a dissociation step was additionally included.

Immunoblot Assay

Total $2 \times 10^5$ cells were boiled for 5 minutes in 2×SDS sample buffer (100 mmol/L TrisHCl [pH 6.8], 4% SDS, 0.2% bromophenol blue, 20% glycerol, and 200 mmol/L β-mercaptoethanol), and then subjected to SDS-PAGE and Western blotting. To detect the TERT, the cells were cultured in 2×SDS sample buffer for 15 minutes at 55° C. TERT-specific (1:300, Rockland Immunochemicals, Gilbertsville, Pa., USA; 600-401-252), AKT-specific (1:1000, Cell Signaling Technology; #9272), phospho-AKT-specific (1:2000, Cell Signaling Technology; #4060), GAPDH-specific (1:2000, Santa Cruz Biotechnology; sc-47724), or β-actin-specific (1:2000, Sigma-Aldrich, St. Louis, Mo., USA; A5441) antibody was diluted in 5% skim milk or bovine serum albumin with TBS-Tween 20, cultured overnight at 4° C., washed, and cultured with HRP-conjugated secondary antibody (1:1000, Abcam; ab131368, or ab131366). By using FUSION-SOLO imager (Vilber Lourmat, Marne La Vallee, France), a chemical fluorescence image was obtained.

Measurement of Cell Viability

As it has been described before (10), the cell viability was measured by using Cell Titer 96 MTS (Promega). Cells were sewn in an amount of 500 to 1000 cells per well, and then treated for 96 hours at a pharmaceutical concentration as described in each graph. Each analysis was repeated 3 times at least. After plotting the data, $IC_{50}$ values were obtained by using GraphPad software. By using Flexstation 3 multimode plate reader (Molecular Devices), optical density showing formazan production was measured at 490 nm.

Chromatin Immunoprecipitation

As it has been described before (Lim S O, et al. Gastroenterology. 2008; 135: 2128-40, 40 el-8.; Hoffmeyer K, et al. Science. 2012; 336: 1549-54.), several modified ChIP (chromatin immunoprecipitation) tests were carried out. In the presence or absence of a PI3K inhibitor, an AKT inhibitor, or a GSK3β inhibitor, Huh7 cells were cultured for 4 days with or without a treatment of 300 μmol/L $H_2O_2$. Under mild shaking for 20 minutes at room temperature, the cells were fixed by using 1% paraformaldehyde. After that, the cells were rinsed twice with ice-cold PBS; resuspended with 400 μL of micrococcal nuclease buffer (50 mmol/L TrisHCl [pH 8.0], 5 mmol/L CaC12, 100 μg/mL BSA, 10 mmol/L KCl, and protease inhibitor cocktail [Roche, Basel, Switzerland; 4693159001]); and disrupted with 2 mm-diameter zirconium beads (Watson); to have micrococcal nuclease digestion (New England Biolabs, Beverly, Mass., USA; M0247S). Chromatin (150 μg) was collected and diluted in a dilution buffer (0.1% NP-40, 2 mmol/L EDTA, 150 mmol/L NaCl, 20 mmol/L TrisHCl [pH 8.0], protease inhibitor cocktail [Roche]), and a phosphatase inhibitor cocktail [Calbiochem]), and then subjected to pre-clearing with 2 μg digested salmon sperm DNA, 10 μL preimmune serum (Santa Cruz Biotechnology; sc-2027), and Dynabeads Protein G (Life Technologies; 1004D) for 2 hours at 4° C. After the immunoprecipitation, 20 μL of Dynabeads Protein G were added thereto and the culture was continued for 2 hours. The Dynabeads were washed continuously for 10 minutes with TSE 1 (0.1% SDS, 1% Triton X-100, 2 mmol/L EDTA, 20 mmol/L TrisHCl, and 150 mmol/L NaCl), TSE II (0.1% SDS, 1% Triton X-100, 2 mmol/L EDTA, 20 mmol/L TrisHCl, and 500 mmol/L NaCl), and buffer III (0.25 mol/L LiCl, 1% NP-40, 1% deoxycholate, 1 mmol/L EDTA, and 10 mmol/L TrisHCl). After that, the beads were washed 3 times with TE buffer, and extraction was made by using 1% SDS and 0.1 mol/L $NaHCO_3$. To have reverse formaldehyde cross-linking, the elution solution was heated overnight at 65° C. By using NucleoSpin DNA clean-up kit, DNA debris were purified. By using primers specific to the TERT promoter region, the PCR amplified product was quantified by qPCR (ABI 7300; Applied Biosystems, Foster City, Calif., USA). The PCR amplification was normalized against the TERT intron. The primer sequences are as follows: β-catenin interaction site for ChIP (forward primer: TCCCGGGTCCCCGGCCCA (SEQ ID NO:8); reverse primer: CCTCGCGGTAGTGGCT-GCGC (SEQ ID NO:9)) and TERT intron for ChIP (forward primer: TGAGGGCTGAGAAGGAGTGT (SEQ ID NO:10); reverse primer: CACGATAGACGACGACCTCA (SEQ ID NO:11)). For each of the β-catenin interaction site which has been recorded before, 20-22 bp were added. The antibodies that are used are as follows: rabbit polyclonal anti-β-catenin (1:200, Abcam, Cambridge, Mass., USA; ab6302), mouse monoclonal anti-RNA polymerase II (1:50, Covance, Princeton, N.J., USA; MMS-126R), and rabbit polyclonal anti-SETD1A (1:100, Novus Biologicals, Littleton, Colo., USA; NBP1-81513).

In Vivo Tumorigenicity Analysis

The animal test was carried out according to the protocol which has been approved by Seoul National University Institutional Animal Care and Use Committee (Approval number: SNU-130225-6). The mouse was kept under usual conditions (i.e., semi-specific pathogen-free state), and allowed to have free access to food and water. For all xenografting studies, 5-week old KSN/Slc nude mouse was used. A mouse with bodyweight of 18 g to 20 g was used for the test. For the xenografting analysis, mock-treated $1\times10^5$ Huh7, $1\times10^5$ Huh7 treated only with 300 μmol/L $H_2O_2$, and $1\times10^5$ Huh7 treated with both of 25 μmol/L idelalisib and 300 μmol/L $H_2O_2$ were washed, harvested in PBS not containing $Ca^{2+}$ or $Mg^{2+}$, and subsequently injected in an amount of 0.2 mL to subcutaneous tissues. According to caliper measurement of two vertical diameters of a tumor (i.e., D1 as largest diameter and D2 as smallest diameter), the tumor product was monitored every week. The tumor volume was calculated by $n\times D1\times D2^2/6$.

Statistical Analysis

Statistical significance of the telomere length measurement and survival ratio was evaluated by Fisher's exact test and log-rank test, respectively. P value for comparison of telomere activity and messenger RNA expression level between the mock and ROS or PI3K-AKT inhibitor treatment was calculated by using a two-sided test. Normality of the frequency distribution was tested by using Shapiro-Willk test. The statistical analysis was carried out by using R software (www.r-project.org) or Prism GraphPad Software version 4.0 (GraphPad Software Inc, San Diego, Calif., USA). All tests were carried out at least three times, independently. The significance value was set as follows: *P<0.05, P<0.01, and *P<0.001.

Example 1. Determination of Inhibition by Idelalisib as PI3K-Akt Inhibitor on HCC Cell Proliferation, TERT Expression, and Telomere Length Maintenance Due to the activity of blocking PI3K-AKT signal transduction, idelalisib as a selective p110δ kinase inhibitor has been used for the treatment of a patient having chronic lymphocytic leukemia (Yang Q, et al. Clin. Cancer Res. 2015; 21: 1537-42; Fruman D A, et al. Nat Rev Drug Discov. 2014; 13: 140-56). In order to measure the activity of idelalisib in liver cells in which p110δ is latently present at different levels, the inventors of the present invention carried out a proliferation assay by using three liver cell lines. Those liver cell lines include Huh7 cells and Hep3B cells which originate from a patient with early HCC and exhibit p110δ at high level (FIGS. 1A and B), and also THLE-3 cell line which is a immortalized human liver epithelial cell line originating from normal primary cells shown in normal adult liver endothelial cells and exhibiting p110δ at low level (FIG. 1C).

Determination was made to see whether or not idelalisib inhibits the cell proliferation of the two HCC cell lines in a concentration-dependent manner. As a result, it was shown that the cell proliferation of the above cell lines was inhibited (FIGS. 1A and 1B). $IC_{50}$ of Huh7 and Hep3B was lower than 30 μmol/L (FIGS. 1A and B) and $IC_{50}$ of THLE-3 cell was higher than 200 μmol/L (FIG. 1C). In addition to the inhibition on cell proliferation, the inventors of the present invention also examined the inhibition of AKT phosphorylation in the two HCC cell lines (FIGS. 1D and E). The basal level AKT phosphorylation was low in THLE-3, and it was not reduced by idelalisib at a concentration of 25 μmol/L (FIG. 1F), indicating that the AKT signal transduction is inactivated in those cells.

Determination was also made to see whether or not idelalisib can reduce the TERT expression and telomere length in HCC cells. It was shown that the TERT expression is reduced in the two HCC cell lines by idelalisib (FIGS. 1D and E) but not in the THLE-3 cells (FIG. 1F). As it is the same as the result showing reduced TERT expression, the telomere length of HCC cells is reduced by idelalisib (FIGS. 1G to 1K). Basal level of the TERT expression was low in the THLE-3 cells and both of the TERT expression and telomere length were not reduced in the THLE-3 cells by idelalisib (FIGS. 1F, 1L and 1M). These results indicate that, upon the activation of PI3K-AKT signal transduction, TERT expression is regulated and it is inhibited by idelalisib in HCC cells but not in THLE-3 cells. Namely, it means that, in the presence of a PI3K inhibitor, cells with activated PI3K-AKT signal transduction become a suitable target for having reduced TERT expression and reduced telomere length.

Example 2. Determination of Inhibition by Idelalisib on TERT Up-Regulation Induced by ROS and Telomere Elongation in HCC Cells It has been confirmed before that ROS can over-activate the PI3K-AKT signal transduction pathway in cancer cells (Brazil D P, et al. Cell. 2002; 111: 293-303; Li V S, et al. Cell. 2012; 149: 1245-56.). However, it is not known whether or not PI3K isotypes are increased by ROS to induce PI3K-AKT activation. Because the expression of PI3K isotype p110δ is higher in HCC cells than THLE-3 cells (FIG. 1 and FIG. 2A) and idelalisib as a p110δ selective inhibitor can inhibit the pAKT and TERT expression and telomere maintenance only in HCC cells, the inventors of the present invention conducted an experiment to see whether or not the p110δ expression is increased by ROS in HCC cells. Among Class I PI3K isotypes (p110α, p110β, p110δ, and p110γ), only p110δ has increased expression in HCC cells after the treatment with hydrogen peroxide ($H_2O_2$) as an ROS inducing agent (FIG. 2B). This result indicates that, through the up-regulation of p110δ expression, ROS over-activates the PI3K-AKT signal transduction, in particular.

Next, in order to examine whether or not ROS can increase the TERT expression and telomere length based on AKT activation, the inventors of the present invention compared the TERT messenger RNA (mRNA) and protein level, and telomere length in cells showing increased ROS level upon treatment with $H_2O_2$ at various concentrations (0 to 300 µmol/L). When compared to the control HCC cells which have not been exposed to $H_2O_2$, the TERT expression and telomere length were increased in the HCC cells which have been treated with 300 µmol/L (telomere length has increased by 25%-30% and TERT expression has increased by 40%-45%; FIGS. 2C and 2D). When the cells were treated simultaneously with N-acetylcysteine (NAC) as ROS scavenger and $H_2O_2$, the $H_2O_2$-induced phenomenon showing increased TERT expression and increased telomere length in HCC cells has disappeared (FIGS. 2C and 2D). With regard to THLE-3 cells, when exposed to 150 µmol/L $H_2O_2$, most cells (85%) did not survive, and the telomere length reduction was shown at this concentration (FIG. 2E). However, there was no change in the TERT expression level, showing the same result as no change in AKT phosphorylation level after $H_2O_2$ treatment (FIG. 2E). These results demonstrate that, according to the up-regulation of AKT phosphorylation and TERT expression, ROS can yield a longer telomere in HCC cells.

In order to study the effect of idelalisib on over-activation of ROS-induced PI3K-AKT signal transduction, the inventors of the present invention measured the TERT expression, telomere length, and telomerase activity in $H_2O_2$-treated HCC cells that are exposed to idelalisib. Compared to the HCC cells treated with $H_2O_2$ only, the TERT expression level and telomere length were significantly lower in the $H_2O_2$-treated HCC cells after a treatment with idelalisib (telomere length was reduced by 40-45% and TERT expression was reduced by 65%-70%; FIGS. 2F and 2G). These results demonstrate that idelalisib inhibits the over-activation of ROS-induced PI3K-AKT signal transduction. Similar to the results of TERT expression and telomere length (FIGS. 2F to 2H), the telomerase activity was reduced in the two HCC cell lines by idelalisib (FIGS. 2I and 2J), but not in the THLE-3 cells (FIG. 2K). The inventors of the present invention found that the ROS-mediated increase in the TERT expression, telomerase activity, and telomere length is almost completely inhibited by idelalisib (FIGS. 2F to 2K).

Example 3. Determination of In Vivo Inhibition by Idelalisib as PI3K Inhibitor on ROS Activity Relating to HCC Tumor Growth Promotion Inventors of the present invention made an investigation to see whether or not the increased chromatin accessibility in TERT promoter during TERT transcription is related with β-catenin. To do so, by using intrinsic β-catenin and an antibody against histone methyl transferase SetD1A which has been reported to promote the TERT transcription based on chromatin remodeling, chromatin immunoprecipitation was carried out. When a PI3K or AKT inhibitor is treated together for chromatin immunoprecipitation, β-catenin and SetD1A, which bind to the TERT promoter in HCC cells, were reduced even in the presence of $H_2O_2$ (FIGS. 3A and 3B). However, when the treatment is carried out also with a GSK3β inhibitor, increased binding of β-catenin and SetD1A was shown regardless of a treatment with $H_2O_2$ (FIG. 3C). These results suggest that, as nuclear expression of β-catenin is increased by ROS through the over-activation of PI3K-Akt signal transduction cascade, binding of SetD1A to the TERT promoter is promoted by ROS.

Next, an examination was made to see whether or not idelalisib can have in vivo inhibition of tumor growth. First, after a treatment with $H_2O_2$, the latency time of tumor appearance in nude mouse, which has been injected with HCC cells having over-activated PI3K-AKT signal transduction, was determined. In a nude mouse which has been injected with $1 \times 10^5$ HCC cells treated with $H_2O_2$, the latency time till to have tumor development was 28 days (FIGS. 3D and 3E). In a nude mouse which has been injected with $1 \times 10^5$ HCC cells treated without $H_2O_2$, the average time till to have an occurrence of tumor was 70 days (FIG. 3E). On the other hand, when the injection was made with HCC cells which have been treated with both $H_2O_2$ and idelalisib, tumor was not formed even after 70 days (FIG. 3D). These results indicate that the tumor growth is promoted by ROS, and this ROS activity of promoting tumor growth can be inhibited in vivo by idelalisib as a PI3K inhibitor.

Example 4. Determination of Relationship Between Phenomenon that Higher TERT Expression is Caused in Accordance with Increase in p110δ Expression Level in HCC Tissues and Low Survival Ratio of Patient with Liver Cancer According to the present invention, it has been found that mRNA level of p110δ increases from early HCC tissue to advanced HCC tissues (stage 2 or higher) (FIG. 4A) and it is positively related with the expression of TERT mRNA (FIG. 4B). This result indicates that same primary signal serves as a cause of having increased expression of p110δ and TERT. The high mRNA level of p110δ is related to a low recurrence-free survival ratio (FIG. 4C), and it indicates that high mRNA level expression of p110δ can be a prognostic marker for HCC like high level TERT mRNA, high level ROS, and long telomere length. This means that, according to inhibition of p110δ kinase to block the expression of p110δ mRNA at high level, the pharmaceutical composition of the present invention can inhibit the HCC tumor growth, and it can be effectively used for a treatment of advanced hepatocellular carcinoma, in particular. It is also recognized that, according to specific blocking of the over-activation of ROS-PI3K-AKT-TERT signal transduction, the pharmaceutical composition is useful for treating liver cancer (FIG. 4D).

Exemplary examples of the present invention are explained in detail in the above. However, the scope of the present invention for which protection is sought is not limited to them, and various modifications and improvements that are made by a skilled person in the art using basic concept of the present invention as defined in the following claims are also within the scope of the present invention.

All technical terms that are used herein are used in the same meanings as those commonly understood by a skilled person in the art, unless specifically defined otherwise. Content of every document which is described as a reference document in the present specification is incorporated by reference herein in its entirety.

The invention claimed is:

1. A method for suppressing expression of PI3K isotype p110δ in liver cancer cells including treating the liver cancer cells with 5-fluoro-3-phenyl-2-[(1S)-1-(7H-purin-6-ylamino)propyl]-4(3H)-quinazolinone or a salt thereof.

2. The method according to claim 1, wherein the liver cancer cells have an increased ROS level.

3. A method for inhibiting ROS-PI3K-AKT-TERT signal transduction pathway in liver cancer cells including treating the liver cancer cells with 5-fluoro-3-phenyl-2-[(1 S)-1-(7H-purin-6-ylamino)propyl]-4(3H)-quinazolinone or a salt thereof.

4. A method for treating hepatocellular carcinoma including administering a pharmaceutically effective amount of the compound 5-fluoro-3-phenyl-2-[(1S)-1-(7H-purin-6-ylamino)propyl]-4(3H)-quinazolinone or a pharmaceutically acceptable salt thereof to a subject who is in need of a treatment of hepatocellular carcinoma.

5. The method according to claim 4, wherein the hepatocellular carcinoma is hepatocellular carcinoma having increased ROS level and increased expression of PI3K isotype p110δ.

6. The method according to claim 5, wherein the hepatocellular carcinoma is advanced hepatocellular carcinoma.

7. The method according to claim 6, wherein the advanced hepatocellular carcinoma is hepatocellular carcinoma at stage II or higher stage on the basis of the Edmondson-Steiner grading system as a method for histological grading of tumor differentiation.

8. The method according to claim 4, wherein ROS-PI3K-AKT-TERT signal transduction is inhibited in the subject.

9. The method according to claim 8, wherein the hepatocellular carcinoma is hepatocellular carcinoma having increased ROS level and increased expression of PI3K isotype p110δ.

* * * * *